(12) United States Patent
Sun et al.

(10) Patent No.: US 6,863,687 B2
(45) Date of Patent: Mar. 8, 2005

(54) INTRAOCULAR LENS

(76) Inventors: Ran Sun, 423 Edgebrook Grove NW, Calgary AB (CA), T3A 5T4; Xiu Fang Liu, 423 Edgebrook Grove NW, Calgary AB (CA), T3A 5T4

(*) Notice: Subject to any disclaimer, the term of this patent is extended or adjusted under 35 U.S.C. 154(b) by 0 days.

(21) Appl. No.: 10/248,917

(22) Filed: Feb. 28, 2003

(65) Prior Publication Data

US 2003/0220688 A1 Nov. 27, 2003

Related U.S. Application Data

(60) Provisional application No. 60/359,992, filed on Feb. 28, 2002.

(51) Int. Cl.$^7$ .................................................. A61F 2/16
(52) U.S. Cl. ...................................... 623/6.46; 623/6.49
(58) Field of Search ................................ 623/6.43–6.56

(56) References Cited

U.S. PATENT DOCUMENTS

| | | | |
|---|---|---|---|
| 4,174,543 A | 11/1979 | Kelman | |
| 4,568,347 A | 2/1986 | Reichert, Jr. | |
| 5,716,403 A | * 2/1998 | Tran et al. | 623/6.46 |
| 5,928,282 A | 7/1999 | Nigam | |
| 6,051,024 A | 4/2000 | Cumming | |
| 6,190,410 B1 | 2/2001 | Lamielle et al. | |
| 6,419,697 B1 | * 7/2002 | Kelman | 623/6.43 |
| 6,482,229 B1 | * 11/2002 | Gwon et al. | 623/6.43 |
| 6,656,223 B2 | * 12/2003 | Brady | 623/6.46 |
| 2002/0103535 A1 | * 8/2002 | Portney | 623/6.18 |
| 2002/0128710 A1 | * 9/2002 | Eggleston | 623/6.22 |
| 2002/0173846 A1 | * 11/2002 | Blake et al. | 623/6.18 |
| 2003/0018386 A1 | * 1/2003 | Laguette et al. | 623/6.46 |

* cited by examiner

Primary Examiner—David H. Willse
Assistant Examiner—Suzette J. Jackson
(74) Attorney, Agent, or Firm—Bennett Jones LLP

(57) ABSTRACT

An IOL described herein includes an optic and at least a first haptic and a second haptic connected to the optic and extending outwardly therefrom; each haptic is formed with either a frog leg configuration or a running leg configuration, which include a base adjacent the optic, a distal foot portion and an intermediate portion connected between the base and the distal foot, the base being connected to the intermediate portion through a first flexible elbow having an angle in a first circumferential direction relative to the to optic and the intermediate portion being connected to the distal foot portion by a second flexible elbow having an angle in a circumferential direction opposite to the first circumferential direction.

37 Claims, 5 Drawing Sheets

INTRAOCULAR LENS

BACKGROUND OF INVENTION

The present invention relates to an intraocular lens (IOL) for implantation into an eye to correct refractive error.

An IOL is a surgical device that can be implanted into the eye to replace cloudy natural lens during cataract surgery or can be implanted into the anterior chamber of the eye to correct refractive errors such as myopia, hyperopia and astigmatism.

IOLs have been available for many years for implantation in both anterior and posterior chambers to correct refractive error. The IOL includes an optic held in position in the eye by means of haptics. Previous IOL designs included an optic and two oppositely extending shaped haptics including C-loops or J-loops or a plate-shaped haptic. Optic and haptics can be made as separate pieces attached together or as one-piece of the materials such as polymers including, for example, polymethylmethacrylate (PMMA) or polypropylene or other foldable materials such as silicone, hydrogel or acrylic.

Haptic design is critical for maintaining lens stability, centralization and flexibility. Major fibrosis forces occur after implantation of the IOL and can cause dislocation and tilting of the lens. Stability is therefore an important factor to avoid the need for surgery to reposition the lens. With respect to flexibility, it is desirable that the lens be foldable for insertion to the eye using an injector or forceps through a small incision and then expandable when positioned in the eye.

SUMMARY OF INVENTION

The IOL of this invention utilizes a bionics concept for configuration of the haptic. Thus, the haptic provides a strong and stable jointed function that can provide the IOL with maximal stability and centralization in the eye. Thus, in accordance with one aspect of the invention, there is provided an intraocular lens comprising: an optic; a first haptic and a second haptic connected to the optic and extending outwardly therefrom; each haptic including a base adjacent the optic, a distal foot portion and an intermediate portion connected between the base and the distal foot, the base being connected to the intermediate portion through a first flexible elbow having an angle in a first circumferential direction relative to the to optic and the intermediate portion being connected to the distal foot portion by a second flexible elbow having an angle in a circumferential direction opposite to the first circumferential direction.

The optic can be sized and formed in various ways, as desired, for the various uses of intraocular lens. For example, the lens optic can be enlarged for anterior chamber implantation because larger diameter optics can reduce halo and glare effects over smaller diameter optics. In one embodiment, the optic is formed to reduce postoperative complications, as by forming the edge with sharp corners to reduce migration of epithelial cells and, thereby, to reduce postoperative capsular opacification.

The lens can be made from any clear materials such as polymethylmethacrylate (PMMA) or polypropylene, but is preferably made to be soft, foldable and resilient, for example, formed of silicone, hydrogel or acrylic. The optic can include a photo-chromatic feature, so that it becomes darker when coming in contact with bright light. This feature could eliminate the need to wear sunglasses and, consequently, it may reduce the possibility of retina damage from the sun.

The haptics can be formed separately from the optic and connected thereto or, alternately, the haptics can be formed integral with the optic to form a one-piece intraocular lens.

The haptics can have a haptic angle parallel to a plane passing through the edges of the optic (i.e. 0°) or slightly offset from the plane.

The flexible elbows in the haptics form joints permitting flex between the parts of the haptics. However, preferably the haptics are each formed as one-piece, being continuous across the flexible elbows rather than of separate, connected parts. Preferably, each of the base and the intermediate portion are formed to define a longitudinal axis therethrough and the first flexible elbow creates a distinct bend in the haptic. The base can be formed thicker, having a greater cross sectional area, than the intermediate portion. The base can taper in cross sectional area from its end adjacent the optic to the end connected to the intermediate portion. In one embodiment, the base is oval in cross sectional shape, while the intermediate has a round shape in cross section.

Preferably, the base also extends out from the optic at an angle other than 90° from the tangent of the optic taken at the base, such that the base does not extend directly radially outwardly from the optic and there is also some flex at this junction.

The second flexible elbow between the distal foot portion and the intermediate portion creates a distinct bend in the haptic at the point of the second flexible elbow.

In one embodiment, the distal foot portion includes one or more segments. At least one of the segments is formed to define a longitudinal axis therethrough. In another embodiment, the distal foot portion is arcuate in shape.

The size of the angles at the first flexible elbow and the second flexible elbow can be varied to achieve a selected degree of flex in the haptic. As noted hereinbefore the haptics can be formed with consideration to bionics. As such, in one embodiment, the haptic is formed with a frog leg design, wherein the first flexible elbow has an angle substantially equal to the second flexible elbow, such that the distal foot portion is positioned radially outwardly from the base. In another embodiment, the angle of the first flexible elbow is greater than the angle of the second flexible elbow such that the haptic is formed with a running leg configuration.

BRIEF DESCRIPTION OF DRAWINGS

A further, detailed, description of the invention, briefly described above, will follow by reference to the following drawings of specific embodiments of the invention. These drawings depict only typical embodiments of the invention and are therefore not to be considered limiting of its scope. In the drawings.

DETAILED DESCRIPTION

Figure 1A:
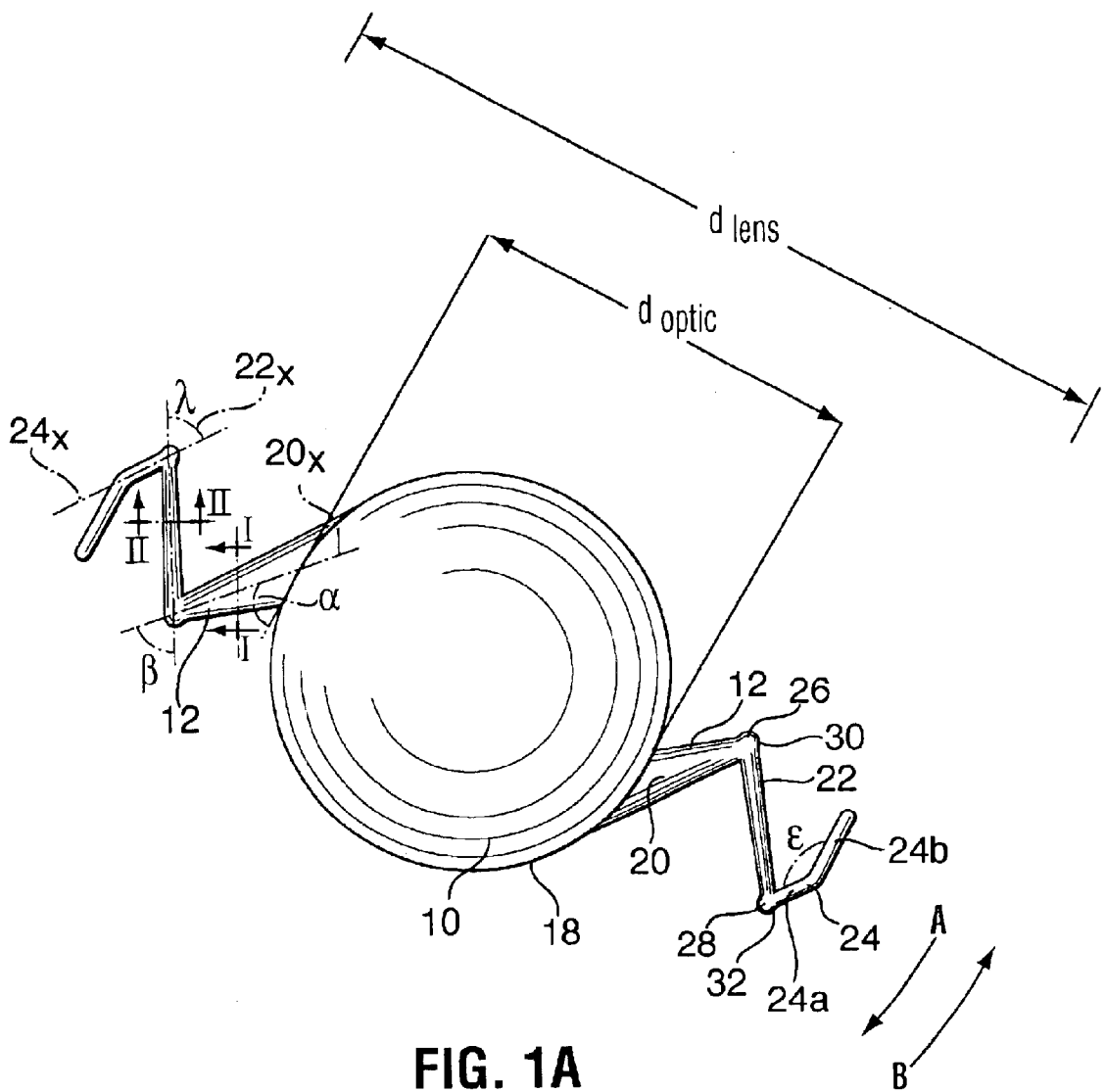
FIG. 1A is a front elevation view of one intraocular lens according to the present invention, the haptic of the lens being frog leg shaped.
Figure 1C:
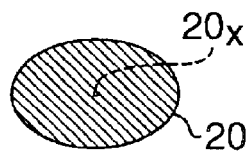
FIG. 1C is a sectional view along line I—I of FIG. 1A.
Figure 1D:
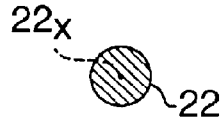
FIG. 1D is a sectional view along line II—II of FIG. 1A.
Figure 1B:
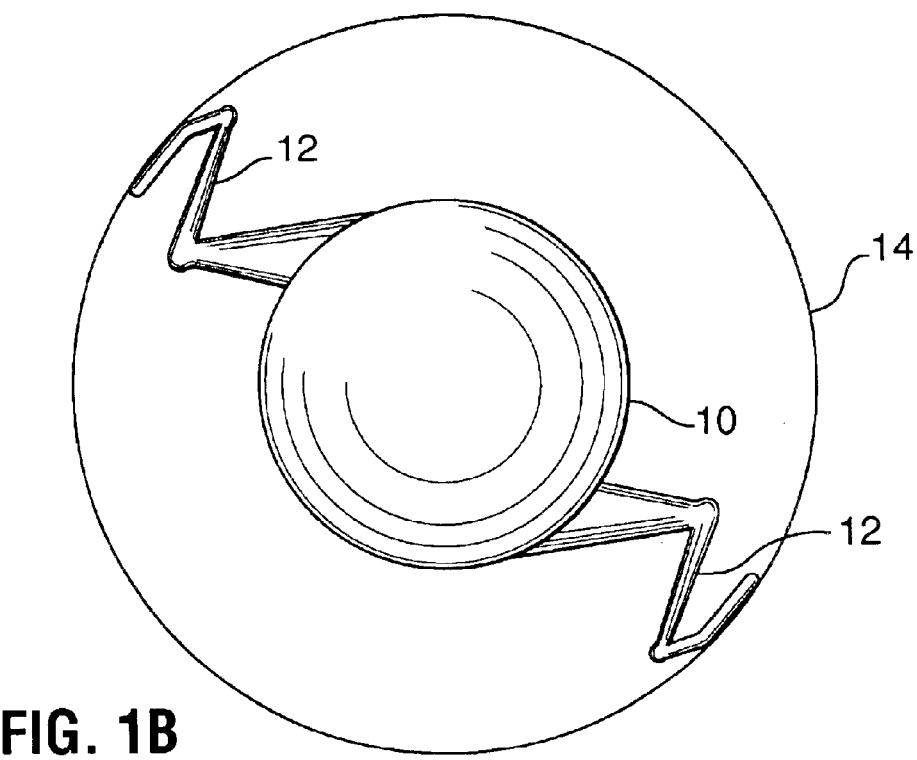
FIG. 1B is a front elevation view of the lens of FIG. 1A in position in a capsular bag.
Figure 2B:
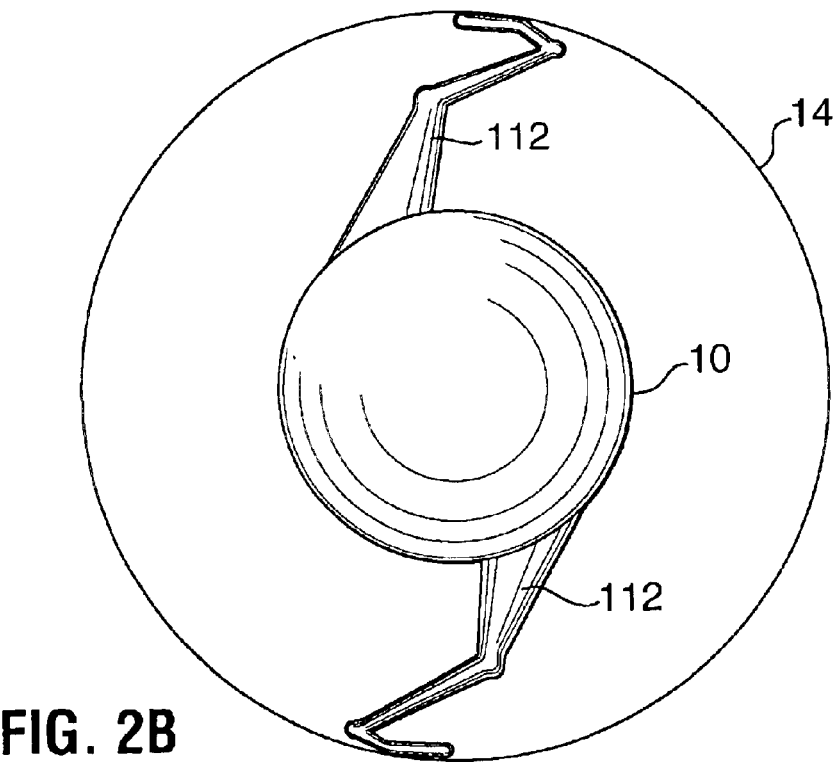
FIG. 2B is a front elevation view of the lens of FIG. 2A in position in a capsular bag.

With reference to FIGS. 1A to 1E, an IOL of the present invention includes an optic 10 and two haptics 12 or more extending outwardly from the optic. The IOL is implantable into the capsular bag 14 of the eye wherein the optic acts as the natural lens providing for refractive vision correction and the haptics centralize and stabilize the optic. The haptics and optic, therefore, are sized to provide an effective diameter $d_{lens}$ to extend across the eye capsule for example between 12 and 15 mm. Haptics 12 are positioned relative to the optic and to each other to react forces tending to decentralize and dislodge the IOL. The haptics are therefore, often positioned and configured reverse-symmetrically about the optic. Thus, in this discussion we may describe only one haptic, with it being understood that the other haptic is substantially the reverse mirror image thereof.

Optic 10 and haptics 12 are preferably formed as a one-piece device of foldable, clear material such as silicone, acrylic, hydrogel or combinations thereof. The optic can be solid or filled. In one embodiment, the optic includes a photo-chromatic element, which tends to darken the lens in response to exposure to bright, outdoor light. This is useful in addressing light sensitivity in patients having undergone cataract surgery and IOL implantation and can avoid the need to wear sunglasses.

Optic 10 includes curved portion 16 and an edge 18 thereabout, which can have rounded or sharp corners, with consideration to factors such as the effect of sharp corners on inhibiting epithelial cell migration.

The optic can be sized, as desired, for a particular use. In particular, the optic can be, for example, 5.5 to 6.0 mm in diameter $d_{optic}$ and useful for a posterior chamber lens or larger such as, for example, 6.0 to 6.5 mm and intended for use in the anterior chamber.

In the illustrated embodiment of FIG. 1, the haptics are formed, with consideration as to bionics terminology, with a frog-leg configuration. Each haptic includes a base 20 adjacent the optic, an intermediate portion 22 and a distal foot portion 24. A first flexible elbow 26 is positioned between base 20 and intermediate portion 22 and a second flexible elbow 28 is positioned between intermediate portion 22 and foot portion 24. First flexible elbow 26 is configured to angle intermediate portion 22 in a first circumferential direction, arrow A, relative to the lens, while second flexible elbow 28 is configured to angle foot 22 in an opposite circumferential direction, arrow B, relative to the lens such that the foot is positioned radially outwardly from, while remaining in plane with, base 20. This arrangement permits in plane flex of the haptic about the elbows 26, 28. While the material of the haptics at the elbows is preferably continuous, the elbows are movable creating flex points along the haptics. A rounded portion 30, 32 on the outside angle of each elbow appear to facilitate flexing movement.

Base 20 is the longest portion of the haptic. The base can be formed as an oval in cross-section, widest in plane with the optic, and tapering from its optic-contact end to its joint end. The intermediate portion and foot are each preferably formed with generally circular cross sections. The intermediate portion preferably tapers toward its foot-contact end.

In the illustrated embodiment, the base and the intermediate portion are each substantially linear, having long axis 20x and 22x, respectively. In addition, distal foot portion 24 has a liner portion with a long axis of 24x. The base extends at an angle α of about 50°–60° between axis 20x and a tangent to edge 18 of the optic. At elbow 26, the intermediate portion extends from the base at an angle β of about 65°–75°. At elbow 28, there is an angle γ of about 65° to 70°, which angles the distal foot portion back such that it is radially outwardly from the base.

In the illustrated embodiment, the foot portion includes two integral segments 24a, 24b. The first foot segment 24a is angularly offset from the second segment 24b by about 145°–150°. Further in-plane flex is provided at the junction between the two foot segments.

Figure 1E:
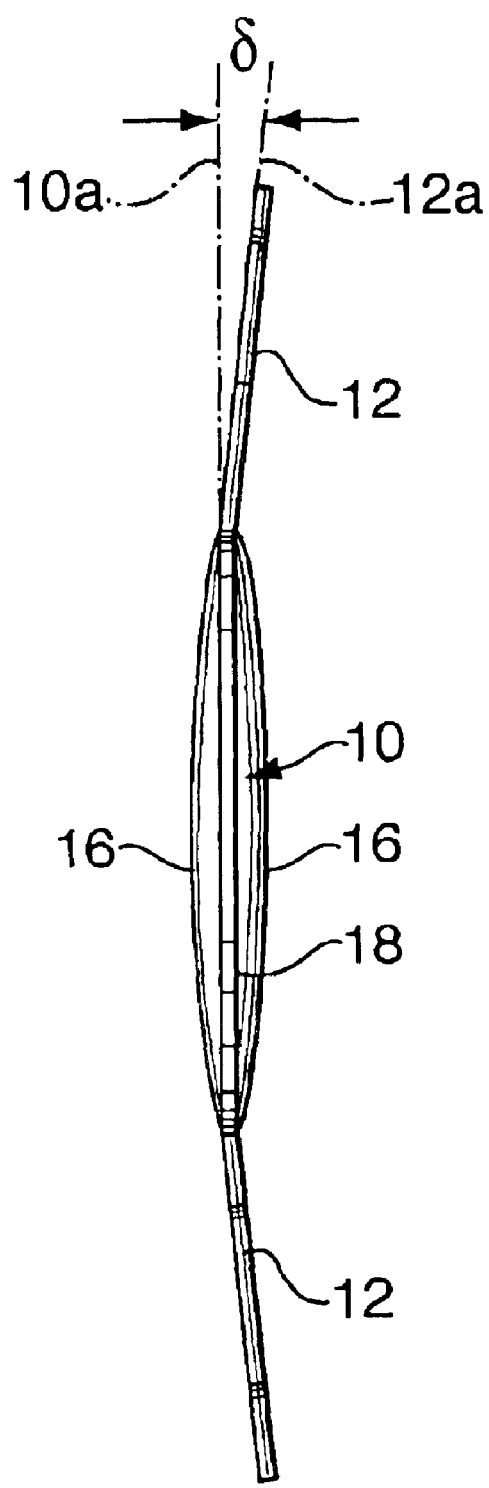
FIG. 1E is a side view of the lens of FIG. 1A.

The haptic angle δ, which is the angle between the center plane 10a through edges 18 and the plane 12a of the haptic, of this lens is about 5°, as shown in FIG. 1E. However, it is to be appreciated that the haptic angle can be reduced such that the haptic is closer to being in plane with the edges of the optic.

Since the lens, including optic 10 and haptics 12 is made as a one-piece device of foldable material, the lens can be folded and inserted into the capsular bag 14 using an injector or forceps through a small incision. After implantation, the lens will unfold and resume its shape with the second foot segments 24b in contact with the capsule and the haptics providing the lens with good centralization and stabilization in the eye.

Referring to FIG. 2, another intraocular lens according to the present invention is shown. The lens includes an optic 10, as set out hereinabove, and two or more haptics 112 extending outwardly from the optic. Again, the intraocular lens is implantable into the capsular bag 14 of the eye wherein the optic acts as the natural lens providing for refractive vision correction and the haptics centralize and stabilize the optic.

Optic 10 and haptics 112 are preferably formed as a one-piece device of foldable, clear material such as silicone, acrylic, hydrogel or combinations thereof.

In the illustrated embodiment of FIG. 2, haptics 112 are formed, with consideration as to bionics terminology, with a running-leg configuration. Each haptic includes a base 120 adjacent the optic, an intermediate portion 122 and a distal foot portion 124. A first flexible elbow 126 is positioned between base 120 and intermediate portion 122 and a second flexible elbow 128 is positioned between intermediate portion 122 and foot portion 124. This arrangement permits in plane flex of the haptic about the elbows 126, 128. While the material of the haptics at the elbows is preferably continuous, the elbows are movable creating flex points along the haptics.

Base 120 is the longest portion of the haptic and tapers from its optic-contact end to its elbow 126 end. The intermediate portion and foot are each preferably formed with generally circular cross sections. The intermediate portion preferably tapers toward its foot contact end.

In the illustrated embodiment, the base is substantially linear having a long axis 120x, respectively. The base extends at an angle α1 of about 70°–75° between axis 120x and a tangent to edge 18 of the optic at the intersection of axis 120x. At elbow 126, the intermediate portion extends from the base at an angle β1 of about 125°–135°. At elbow 128, there is an angle γ 1 of about 40°–45°, which angles the distal foot portion back toward the intermediate portion. Note that first flexible elbow 126 is configured to angle intermediate portion 122 in a first circumferential direction, arrow A, relative to the optic, while second flexible elbow 128 is configured to angle foot 122 in an opposite circumferential direction, arrow B, relative to the optic, while remaining in plane with base 120.

In the illustrated embodiment, the foot portion includes two integral segments 24a, 24b. The first foot segment 24a is angularly offset from the second segment 24b by an angle of about 150–155°. Further in-plane flex is provided at the junction between the two foot segments.

Figure 2E:
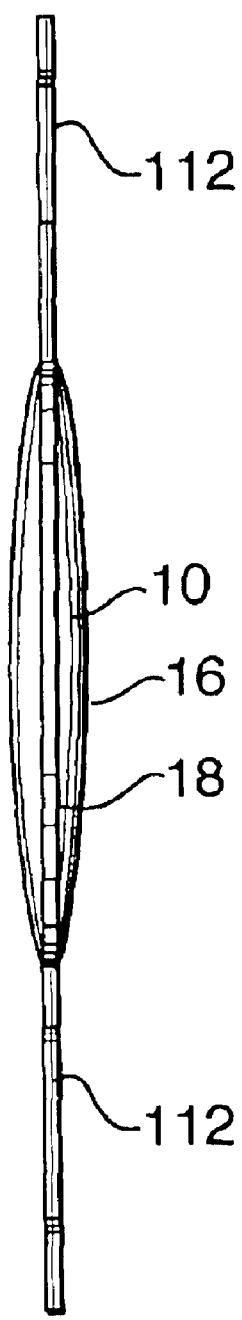
FIG. 2E is a side view of the lens of FIG. 2A.
Figure 2A:
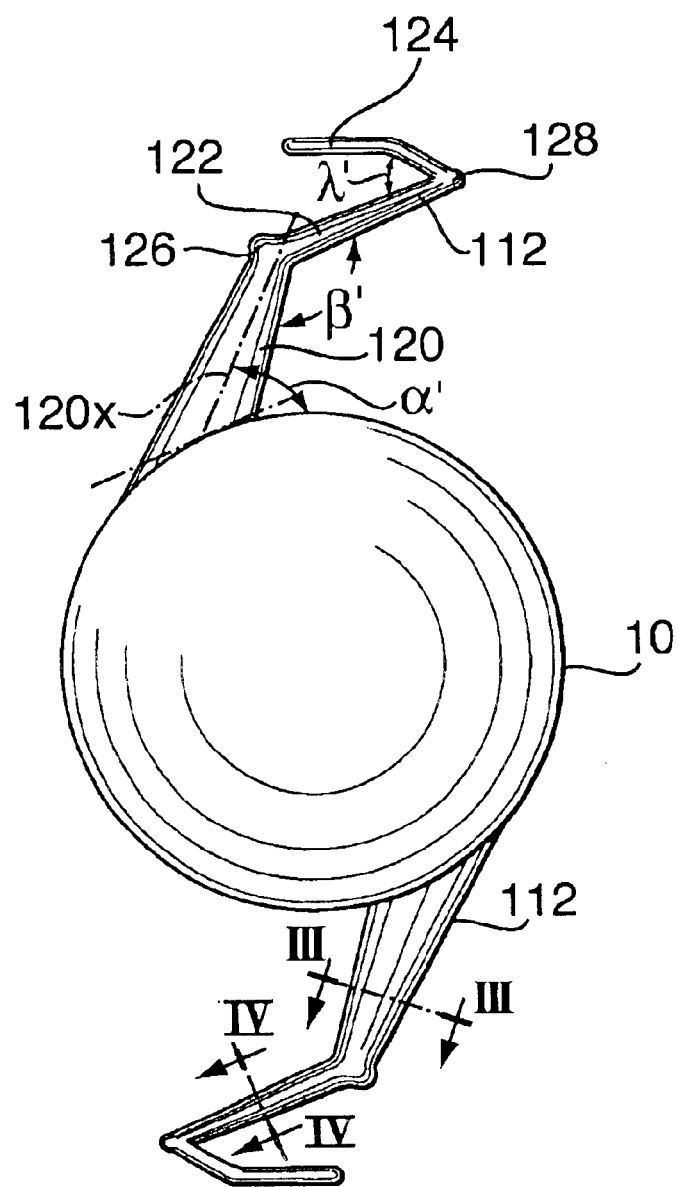
FIG. 2A is a front elevation view of one intraocular lens according to the present invention, the haptic of the lens having a running leg configuration.
Figure 2C:
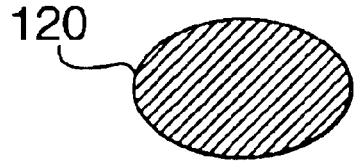
FIG. 2C is a sectional view along line III—III of FIG. 2A.
Figure 2D:
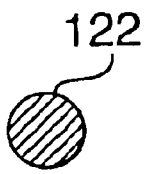
FIG. 2D is a sectional view along line IV—IV of FIG. 2A.

The haptic angle of this lens is about 0°, as shown in FIG. 2E. Again, it is to be appreciated that the haptic angle can be adjusted as desired.

Figure 3A:
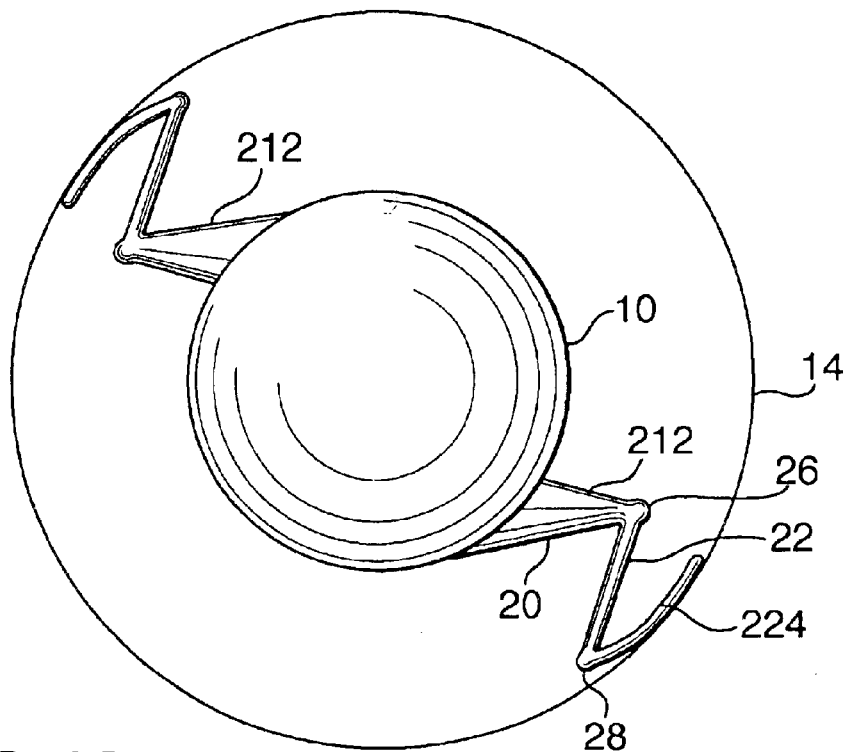
FIG. 3A is a front elevation view of another intraocular lens according to the present invention.

Referring to FIG. 3, further IOLs according to the present invention are shown. The lens each include an optic 10 and two or more haptics 212, 312 extending outwardly from the optic. The haptics of the lens of FIG. 3A have a frog leg configuration including a base 20 adjacent the optic, an intermediate portion 22 and a distal foot portion 224. A first flexible elbow 26 is positioned between base 20 and intermediate portion 22 and a second flexible elbow 28 is positioned between intermediate portion 22 and foot portion 224. Foot portion 224 is arcuate in plane with the haptic. The foot portion can be lengthened, as desired, to provide extra stability in the capsular bag 14.

Figure 3B:
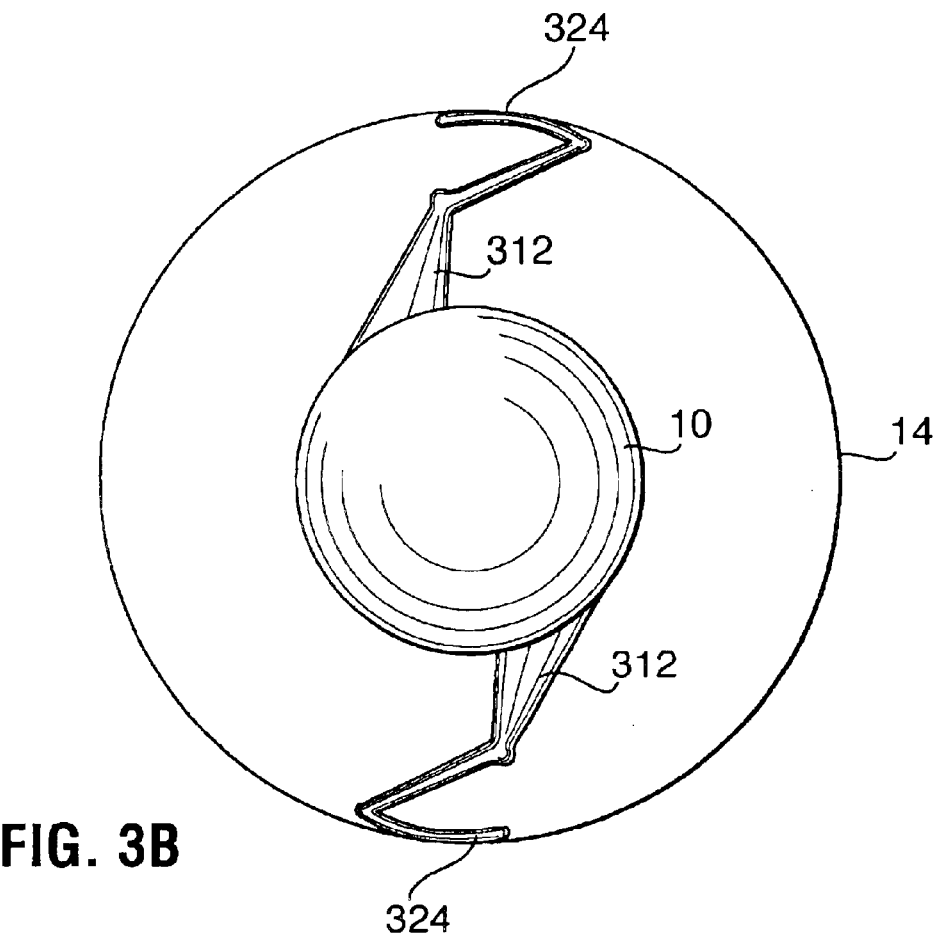
FIG. 3B is a front elevation view of another intraocular lens according to the present invention.

Haptics 312 of the lens shown in FIG. 3B also has a foot portion 324 shaped arcuately in plane with the haptic and lengthened to provide stability in the capsular bag 14.

It will be apparent that these and many other changes may be made to the illustrative embodiments, while falling within the scope of the invention, and it is intended that all such changes be covered by the claims appended hereto. γ

What is claimed is:

1. An IOL comprising: an optic; a first haptic and a second haptic connected to the optic and extending outwardly therefrom; each haptic including a base adjacent the optic, a distal toot portion and an intermediate portion connected between the base and the distal foot, the base being connected to the intermediate portion through a first flexible elbow having an angle in a first circumferential direction relative to the to optic and the intermediate portion being connected to the distal foot portion by a second flexible elbow having an angle in a circumferential direction opposite to the first circumferential direction, wherein an outside angle of at least one of the first flexible elbow and the second flexible elbow includes a rounded, protruding portion.

2. The IOL of claim 1 wherein the optic includes a photo-chromatic feature such that it becomes darker when coming in contact with bright light.

3. The IOL of claim 1 wherein the haptics are formed integral with the optic.

4. The IOL of claim 1 formed of a foldable material.

5. The IOL of claim 1 formed of a material selected from the group consisting of PMMA or polypropylene.

6. The IOL of claim 1 wherein the haptics are each formed in one-piece and continuous across the flexible elbows.

7. The IOL of claim 1 wherein each of the base and the intermediate portion are formed to define a longitudinal axis therethrough and the first flexible elbow creates a distinct bend in the haptic.

8. The IOL of claim 1 wherein the bass has an oval shape in cross section and the intermediate portion is round in cross section.

9. The IOL of claim 1 wherein the base tapers in cross sectional area from its end adjacent the optic to its end connected to the intermediate portion.

10. The IOL of claim 1 wherein the second flexible elbow between the distal foot portion and the intermediate portion creates a distinct bend in the haptic at the point of the second flexible elbow.

11. The IOL of claim 1 wherein the distal foot portion includes at least two segments.

12. The IOL of claim 1 wherein the distal foot portion is formed arcuately in plane with the haptic.

13. The IOL of claim 1 wherein the first haptic is formed with a frog leg configuration, wherein the first flexible elbow has an angle substantially equal to the second flexible elbow and the distal foot portion is positioned radially outwardly from the base.

14. The IOL of claim 1 wherein the first haptic is formed with the angle of the first flexible elbow being greater than the angle of the second flexible elbow such that the haptic is formed with a running leg configuration.

15. An IOL comprising: an optic; a first haptic and a second haptic connected to the optic and extending outwardly therefrom; each haptic including a base that is oval in cross section adjacent the optic, a distal foot portion and an intermediate portion that is round in cross section connected between the base and the distal foot, the base being connected to the intermediate portion through a first flexible elbow having an angle in a first circumferential direction relative to the optic and the intermediate portion being connected to the distal foot portion by a second flexible elbow having an angle in a circumferential direction opposite to the first circumferential direction.

16. The IOL of claim 15 wherein the haptics are formed integral with the optic.

17. The IOL of claim 15 formed of a foldable material.

18. The IOL of claim 15 wherein the haptics are each formed in one-piece and continuous across the flexible elbows.

19. The IOL of claim 15 wherein each of the base and the intermediate portion are formed to define a longitudinal axis therethrough and the first flexible elbow creates a distinct bend in the haptic.

20. The IOL of claim 15 wherein an outside angle of at least one of the first flexible elbow and the second flexible elbow includes a rounded, protruding portion.

21. The IOL of claim 15 wherein the base tapers in cross sectional area from its end adjacent the optic to its end connected to the intermediate portion.

22. The IOL of claim 15 wherein the second flexible elbow between the distal foot portion and the intermediate portion creates a distinct bend in the haptic at the point of the second flexible elbow.

23. The IOL of claim 15 wherein the distal foot portion includes at least two segments.

24. The IOL of claim 15 wherein the distal foot portion is formed arcuately in plane with the haptic.

25. The IOL of claim 15 wherein the first haptic is formed with a frog leg configuration, wherein the first flexible elbow has an angle substantially equal to the second flexible elbow and the distal foot portion is positioned radially outwardly from the base.

26. The IOL of claim 15 wherein the first haptic is formed with a running leg configuration wherein the angle of the first flexible elbow is greater than the angle of the second flexible elbow.

27. An IOL comprising: an optic; a first haptic and a second haptic connected to the optic and extending outwardly therefrom; each haptic including a base adjacent the optic, a distal foot portion and an intermediate portion connected between the base and the distal foot, the base being connected to the intermediate portion through a first flexible elbow having an angle in a first circumferential direction relative to the to optic and the intermediate portion being connected to the distal toot portion by a second flexible elbow having an angle in a circumferential direction opposite to the first circumferential direction, wherein the first haptic is formed with a frog leg configuration such that the first flexible elbow has an angle substantially equal to the second flexible elbow and the distal foot portion is positioned radially outwardly from the base.

28. The IOL of claim 27 wherein the haptics are formed integral with the optic.

29. The IOL of claim 27 formed of a foldable material.

30. The IOL of claim 27 wherein the haptics are each formed in one-piece and continuous across the flexible elbows.

31. The IOL of claim 27 wherein each of the base and the intermediate portion are formed to define a longitudinal axis therethrough and the first flexible elbow creates a distinct bend in the haptic.

32. The IOL of claim 27 wherein an outside angle of at least one of the first flexible elbow and the second flexible elbow includes a rounded, protruding portion.

33. The IOL of claim 27 wherein the base tapers in cross sectional area from its end adjacent the optic to its end connected to the intermediate portion.

34. The IOL of claim 27 wherein the second flexible elbow between the distal foot portion and the intermediate portion creates a distinct bend in the haptic at the point of the second flexible elbow.

35. The IOL of claim 27 wherein the distal foot portion includes at least two segments.

36. The IOL of claim 27 wherein the distal foot portion is formed arcuately in plane with the haptic.

37. The IOL of claim 27 wherein the first haptic is formed with a running leg configuration wherein the angle of the first flexible elbow is greater than the angle of the second flexible elbow.

\* \* \* \* \*